United States Patent [19]

Lu

[11] Patent Number: 5,496,350
[45] Date of Patent: Mar. 5, 1996

[54] APPARATUS AND METHOD FOR DETECTING, CONFIRMING AND TERMINATING PACEMAKER MEDIATED TACHYCARDIA

[75] Inventor: Richard Lu, Highlands Ranch, Colo.

[73] Assignee: Telectronics Pacing Systems, Inc., Englewood, Colo.

[21] Appl. No.: 227,306

[22] Filed: Apr. 12, 1994

[51] Int. Cl.⁶ .................................................. A61N 1/365
[52] U.S. Cl. .................................................................. 607/14
[58] Field of Search .......................... 607/14, 9; 128/705

[56] References Cited

U.S. PATENT DOCUMENTS

| 4,686,989 | 8/1987 | Smyth et al. | 607/14 |
| 5,253,644 | 10/1993 | Elmvist | 607/14 |

Primary Examiner—William E. Kamm
Assistant Examiner—Kennedy J. Schaetzle
Attorney, Agent, or Firm—Gottlieb, Rackman & Reisman

[57] ABSTRACT

A pacemaker for automatically confirming the presence of, and terminating, pacemaker mediated tachycardia (PMT). A number of V-pace to A-sense intervals are measured. If the measured intervals are consistent, it is possible that there is retrograde conduction giving rise to PMT. To confirm that the A-senses were not due to noise, atrial premature beats, etc., several ventricular pacing pulses are generated in a manner that eliminates the possibility of atrial beats being due to retrograde conduction; a series of simultaneous atrial and ventricular pacing pulses are generated. If A-senses consistent with the previously measured intervals are not sensed, retrograde conduction is confirmed. The PMT should have been terminated by the simultaneous atrial and ventricular pacing, but in any event the PVARP may be lengthened to exceed the longest measured V-pace to A-sense interval.

30 Claims, 3 Drawing Sheets

APPARATUS AND METHOD FOR DETECTING, CONFIRMING AND TERMINATING PACEMAKER MEDIATED TACHYCARDIA

FIELD OF THE INVENTION

This invention relates to heart pacemakers, and more particularly to the automatic detection, confirmation and termination of pacemaker mediated tachycardia.

BACKGROUND OF THE INVENTION

In my co-pending application entitled "PACEMAKER PROGRAMMER-BASED AUTOMATIC RETROGRADE CONDUCTION MEASUREMENT", Ser. No. 08/226,175 filed on even date herewith, which application is hereby incorporated by reference, there is described a technique by which retrograde conduction in a pacemaker patient may be measured automatically by using a physician-operated pacemaker programmer. The measurement of retrograde conduction intervals allows the setting of an appropriate postventricular atrial refractory period (PVARP) to avoid retrograde conduction which might give rise to the onset of pacemaker mediated tachycardia (PMT).

The existence of retrograde conduction via the natural pathway, and the antegrade conduction via the implanted dual-chamber pacemaker, provide a reentry circuit that mimics the natural situation in which an accessory pathway allows a circus movement tachycardia. This reentry tachycardia, PMT, may occur when a P-wave displaced from its natural position before the QRS complex is tracked in the ventricle. The P-wave can be displaced by a ventricular premature contraction or ventricular stimulus with retrograde conduction. If the displaced P-wave falls within the atrial refractory period, it will not be tracked and no further event will occur. On the other hand, if the displaced P-wave falls outside the atrial refractory period, it will begin an AV interval and be tracked in the ventricle. If retrograde conduction exists, another P-wave will occur following the ventricular stimulus, and the reentry loop will be sustained.

If retrograde conduction exists, PMT can be prevented by programming the PVARP longer than the retrograde conduction interval. The retrograde conduction time begins with a ventricular event. The retrograde conduction time ends when a retrograde P-wave occurs (assuming that the retrograde conduction results in an atrial event). The PVARP interval similarly begins with the ventricular event. Thus, PMT can be prevented by making the PVARP interval longer than the retrograde conduction interval because the atrial event will not be tracked (although it can be sensed) if it occurs during the PVARP. On the other hand, higher tracking rates can be programmed if the PVARP is shortened. Therefore, to provide an optimal trade-off between these two factors, the retrograde conduction interval should be measured if it exists.

My aforesaid co-pending application discloses how a patient's retrograde conduction interval may be measured automatically by using a pacemaker programmer to control cycling of the pacemaker and to display information telemetered from the pacemaker. The pacemaker first generates a series of ventricular pacing pulses, and it measures the interval between each V-pace and the subsequent atrial beat (A-sense). If the measured intervals are consistent, it is possible that there is retrograde conduction. To confirm that the A-senses were not due to noise, atrial premature beats, etc., subsequent ventricular pacing pulses are generated in a manner that eliminates the possibility of atrial beats being due to retrograde conduction: a series of simultaneous atrial and ventricular pacing pulses are generated. If A-senses consistent with the previously measured intervals are not sensed, retrograde conduction is confirmed, i.e., the previously detected A-senses must have been due to retrograde conduction. The PVARP of the pacemaker can then be set to exceed the longest measured V-pace to A-sense (VP-to-AS) interval so that the effect of retrograde conduction is minimized. Any retrogradely conducted signal falls in the PVARP where it is ignored by the pacemaker. Since PMT arises from the sensing, early in the pacemaker cycle, of a retrogradely conducted signal, PMT can be avoided by extended the PVARP so that a retrogradely conducted signal does not trigger the usual AV delay and generation of a ventricular pacing pulse.

The technique disclosed in my aforesaid co-pending application is preferably controlled by a pacemaker programmer. It is an aid to the physician to allow him to set an appropriate PVARP interval to minimize the occurrence of PMT. But if PMT does occur, for example, if the retrograde conduction time changes, it would be highly advantageous not only to confirm its presence in a reliable way, but to automatically terminate it.

SUMMARY OF THE INVENTION

The invention is an apparatus and method for automatically detecting, confirming and terminating pacemaker mediated tachycardia. The underlying methodology is related to that just described for measuring retrograde conduction time.

There are standard techniques in use today for detecting PMT, and any of such techniques can be used with the subject invention to first detect PMT. Preferably, a "sudden onset" in rate within a few beats is a triggering event for suspecting PMT. For example, a rate increase from 80 to 100 beats per minute within three beats is an indication that PMT may be present. The suspicion of PMT may be reinforced if the high rate is some percentage, e.g., 20%, higher than the sensor-indicator rate in rate-response mode, or some percentage higher than the average heart rate prior to sudden onset in non-rate responsive mode. In general, PMT is suspected if sudden onset is accompanied by the rate being higher than the expected physiological rate by a predetermined percentage. In order to confirm the existence of PMT, a technique similar to that described in my copending application is employed, although it is under control of the pacemaker rather than the pacemaker programmer. A number of VP-to-AS intervals are measured. If they are consistent, then the PMT detection process is passed. The next phase, confirmation and termination, involves delivering simultaneous, or approximately simultaneous, atrial and ventricular pacing pulses, or a ventricular pacing pulse simultaneously with an atrial sense. Such pulses minimize the effect of retrograde conduction, i.e., if there is PMT then it should not be exhibited during the cycles in the confirmation and termination process. If no A-senses occur with VP-to-AS intervals consistent with those earlier measured, then it is an indication that the previous short VP-to-AS intervals were indeed due to PMT. The PMT confirmation and termination process is thus very similar to the retrograde conduction confirmation process of my aforesaid application.

At the same time that PMT is confirmed, it is terminated. The reason for this is that the simultaneous contraction of both chambers not only prevents retrograde conduction from triggering an atrial event (because the atria are refractory when the retrograde signal arrives), but results in collisions of the respective wavefronts and blocks retrograde conduction from occurring in the first place. Thus, the PMT should not continue when normal pacing resumes. Nevertheless, to ensure that PMT is prevented, the PVARP is extended as the final step in the overall process. If PMT is detected and confirmed once again, then the PVARP will be extended still further. Preferably, the PVARP is made longer than the longest measured retrograde conduction time in the detection process. (Although not part of the present invention, it is also possible to automatically shorten the PVARP. For example, periodically the retrograde conduction time may be measured as described in my copending application, and the PVARP can be shortened until it is just slightly longer, by an appropriate safety margin, than the longest measured VP-to-AS interval.)

BRIEF DESCRIPTION OF THE DRAWINGS

Further features and advantages of this invention will become apparent upon consideration of the following detailed description in conjunction with the drawing, in which.

DESCRIPTION OF THE INVENTION

Figure 1:
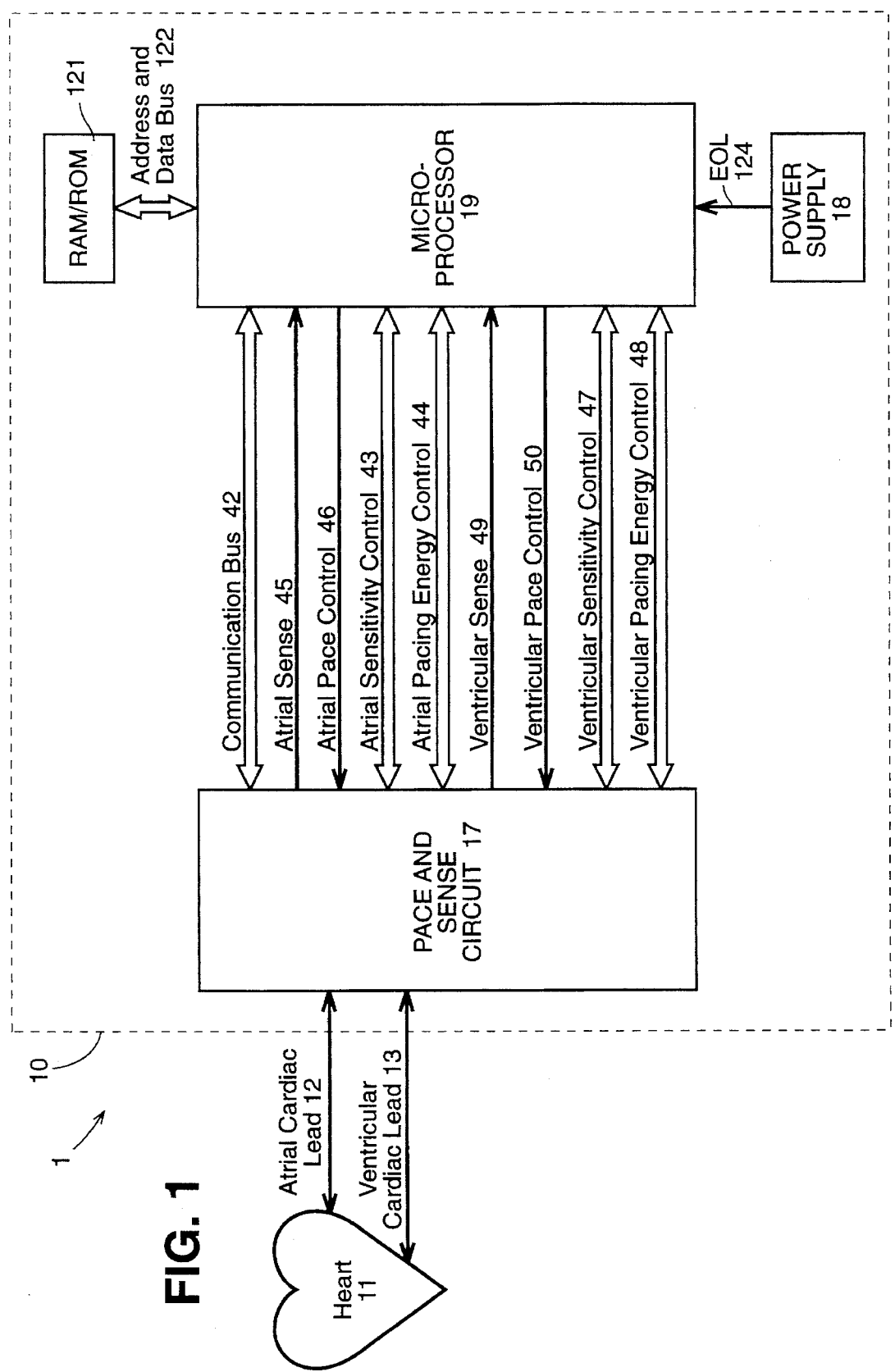
FIG. 1 is a block diagram of the hardware system of the invention.
Figure 2:
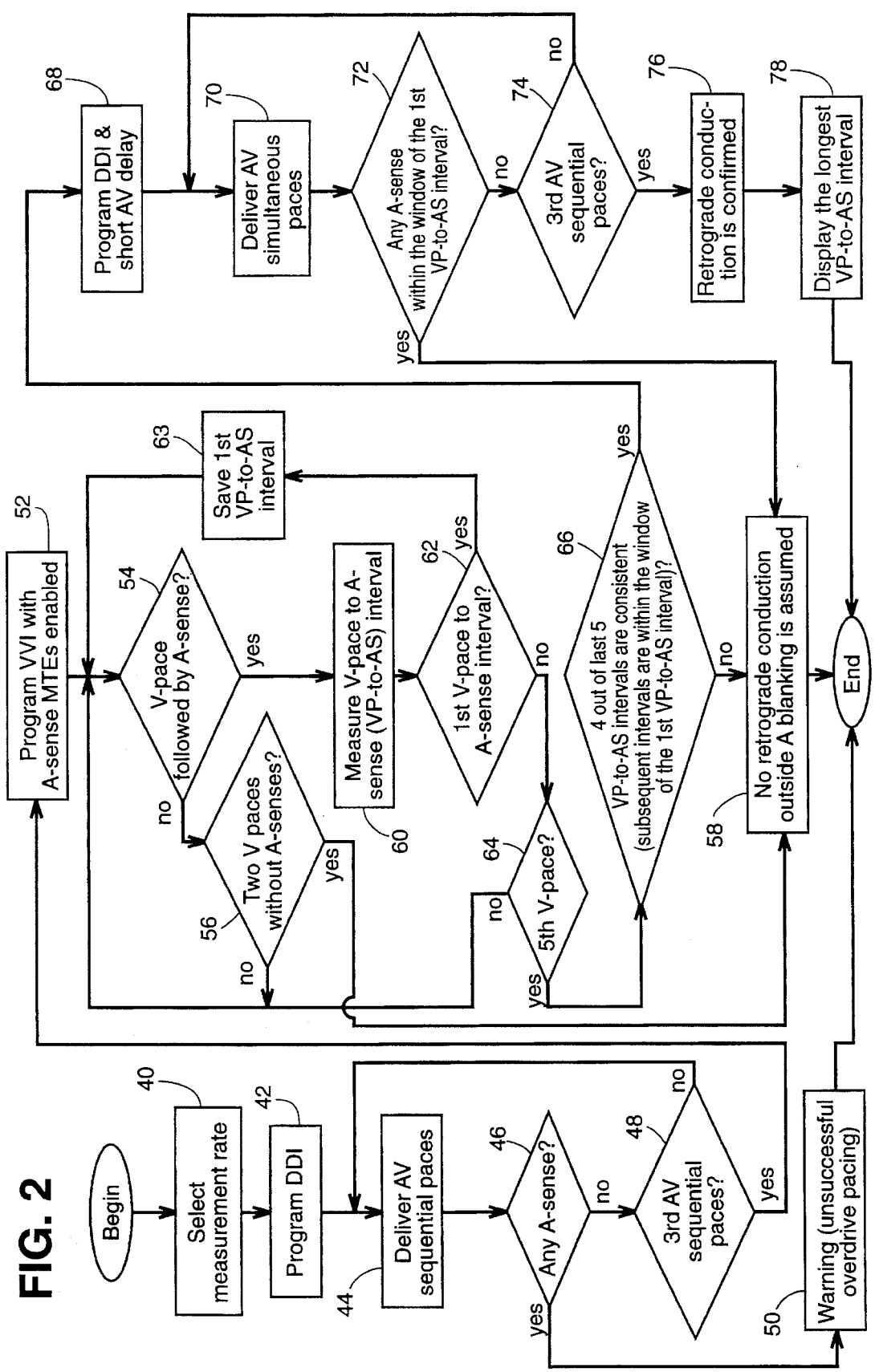
FIG. 2 is the same as FIG. 2 in my aforesaid application, and is a flow chart of the algorithm used with a pacemaker programmer (not shown in this application) to automatically confirm the presence of retrograde conduction and measure its duration.

An illustrative pacemaker in which the subject invention may be implemented is disclosed in the co-pending application of Tibor A. Nappholz entitled "FORCED ATRIO-VENTRICULAR SYNCHRONY DUAL CHAMBER PACEMAKER", Ser. No. 08/226,654, filed on even date herewith and assigned to the assignee of the subject application, now U.S. Pat. No. 5,441,523. FIG. 1 herein is the same as FIG. 1 in the Nappholz application. The only difference is that while in the Nappholz drawing the pace and sense circuit 17 is shown as being represented in detail in FIG. 2 and microprocessor 19 is shown as being represented in detail in FIG. 3, those indications are not included on FIG. 1 herein. FIGS. 1 and 2 of the Nappholz application provide details of pace and sense circuit 17, and microprocessor 19, and the Nappholz application is hereby incorporated by reference. The remaining figures in the Nappholz application completely depict a pacemaker in which the subject invention may be employed. For the purposes of the subject invention, however, it is sufficient to understand just the block diagram of FIG. 1.

The pacemaker 1 is designed to be implanted in a patient and includes a pulse generator 10 and appropriate leads for electrically connecting the pulse generator to the patient's heart 11. The pacemaker includes an atrial cardiac lead 12 extending to the atrium of the patient's heart for the administration of pacing therapy to the atrium, and a ventricular cardiac lead 13 extending to the ventricle of the patient's heart for the administration of pacing therapy to the ventricle. The pulse generator 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a reliable voltage level to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of the approach of battery failure in the power supply 18. The microprocessor 19 and the pace and sense circuit 17 are connected by a communication bus 42, an atrial sense line 45, an atrial pace control line 46, an atrial sensitivity control bus 43, an atrial pacing energy control bus 44, a ventricular sense line 49, a ventricular pace control line 50, a ventricular sensitivity control bus 47, and a ventricular pacing energy control bus 48.

It will be apparent to those skilled in the art that the principles of the subject invention may be applied to any conventional dual-chamber pacemaker. It is therefore to be understood that the system of FIG. 1 is only representative, and that even the full disclosure to be found in the Nappholz application is only illustrative.

Figure 3:
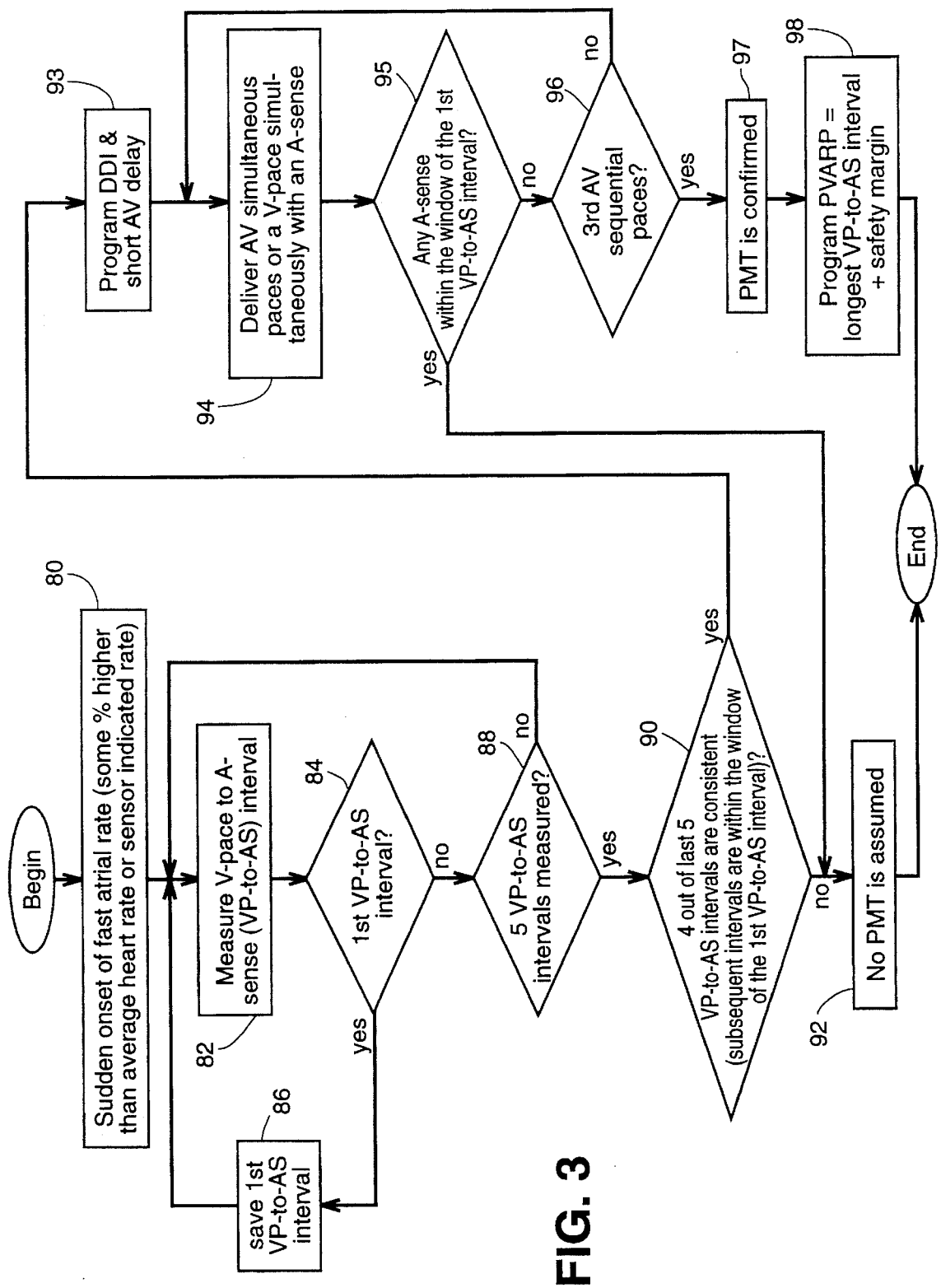
FIG. 3 is a flow chart of the algorithm of the present invention used in the system of FIG. I to detect, confirm and terminate pacemaker mediated tachycardia.

FIG. 2 is the same as FIG. 2 in my aforesaid co-pending application, and it depicts the flow chart for automatically confirming the presence of retrograde conduction and measuring its duration. As laid out on FIG. 2, there are three columns of steps. The leftmost column of steps set up the measurement system and stabilize the beating of the patient's heart. Those steps are not used in the subject invention depicted on FIG. 3. The second and third columns of steps in FIG. 2 are directed to retrograde conduction detection, and confirmation. The method of FIG. 3 is similar, but involves suspicion of PMT, PMT detection, and PMT confirmation and termination. The cycling in the flow chart of FIG. 3 will be readily understood after considering the cycling in the flow chart of FIG. 2.

At the start of the retrograde conduction test procedure, an overdrive measurement rate is selected in step 40 of FIG. 2. Overdrive pacing occurs so that there are no intrinsic beats. In step 42, the pacemaker is programmed to operate in the DDI mode. In step 44, a number of sequential AV pacing pulses are delivered for the purpose of giving rise to stable cycling without any intrinsic beats.

In step 46, a check is made to see whether an atrial event (A-sense) occurs following each pair of atrial and ventricular pulses. (The test for an A-sense is made only outside the atrial channel blanking interval, since the far-field R-wave signal may result in the pacemaker thinking that it has sensed an intrinsic atrial beat if the atrial channel is not blanked for about 150 ms following a ventricular pacing pulse.) If an atrial beat is detected, the physician is informed in step 50 by the programmer that the overdrive pacing has not eliminated intrinsic beats and the test procedure is aborted. The test may be reinitiated with a higher overdrive pacing rate. On the other hand, if following each pair of atrial and ventricular paces an A-sense is not detected in step 46, a check is made in step 48 whether three pairs of pacing pulses have yet been delivered. If they have not, a return is made to step 44 at which time another pair of pacing pulses is generated. When three pairs of atrial and ventricular pulses have been generated without any A-senses having been detected, i.e., the overdrive pacing is successful, and a stable beating action has been set in place, then the actual detection of the retrograde conduction time begins at step 52. The preliminary sequencing discussed thus far is designed primarily to ensure that overdrive pacing is operative, and that there is a stable beating of the patient's heart.

If the overdrive pacing is successful, then in step 52 the pacemaker is programmed to operate in the VVI mode at the previously selected rate, with A-sense MTEs enabled. This in effect gives rise to operation in the VDI mode (atrial and ventricular sensing, but ventricular pacing only). The pacemaker telemeters out to the programmer, for display to the physician, every sensing of an atrial beat, as well as the generation of every ventricular pacing pulse. Following each V-pace, it is determined in step 54 whether an A-sense occurs outside the cross-channel blanking interval. If there is no A-sense following a V-pace, but in step 56 it is determined that this is not the second cycle in which this has happened, then a return is made to step 54 where the same test is performed in the next cycle, for the next V-pace. On the other hand, if there have been two cycles in which V-paces have not been followed by A-senses, it is an indication that there is no retrograde conduction (i.e., no A-senses after atrial blanking), a determination made in step 58. The test procedure comes to an end because most likely there is no retrograde conduction, and therefore no measurement is required.

It is only if an A-sense follows a V-pace, as determined in step 54, that there may be retrograde conduction so that a measurement should be taken. In step 60, the interval between the V-pace and A-sense events is measured. The VP-to-AS interval measured in the first cycle is used as a standard against which subsequent VP-to-AS intervals are compared. If there is retrograde conduction, there should be consistency in the VP-to-AS intervals. In step 62, a check is made to see whether the interval just measured is the first. If it is, then in step 63 the current VP-to-AS interval is registered as the first interval, and it is thereafter used as the standard for subsequent measured intervals. The system then returns to step 54 to await the next cycle.

On the other hand, if the VP-to-AS interval just measured is not the first, then the test in step 66 is performed. It is here that a decision may be made that retrograde conduction is not occurring, and that previously detected A-senses were due to noise or some other cause. The decision is not made that retrograde conduction is occurring. If the possibility of retrograde conduction is not excluded, then it may be present, but it still must be confirmed.

But before step 66 is performed, it must be determined that five V-paces have taken place. This is accomplished in step 64. If five V-paces have not occurred, a return is made to step 54. Otherwise, the "consistency" test in step 66 is performed.

In step 66, each current VP-to-AS interval is compared with the first interval saved in step 63. Any current interval is consistent with the first interval if it is within ±20 ms of the first interval. If four out of the last five intervals are consistent, then retrograde conduction may be occurring, and the system advances to step 68. On the other hand, if four out of the last five measured intervals are not consistent, it is assumed that there is no retrograde conduction because VP-to-AS intervals are generally consistent when there is retrograde conduction. Consequently, in step 58 a determination is made that there is no retrograde conduction interval to measure and the sequence concludes.

Just because a number of P-waves have been sensed at consistent intervals after preceding ventricular paces is not a guarantee that retrograde conduction is really occurring. It may be that noise has been sensed and there is no retrograde conduction. As the preceding sequencing takes place, the longest VP-to-AS interval is registered and, if there is retrograde conduction, than this is the interval which is reported to the physician in step 78—the longest interval is desired because the PVARP should be programmed to exceed this interval. But before the longest interval is reported, a check is made that there really is retrograde conduction. What is done is similar to the initial sequencing—the pacemaker is programmed so that there is almost certainly no retrograde conduction; if A-senses are still detected within the window of the first VP-to-AS interval, then what is really being sensed is most likely noise, not the effects of retrograde conduction.

In step 68, the pacemaker is programmed to the DDI mode with a short AV delay, preferably a delay of 0 ms. With an AV delay of 0 ms (some pacemakers such as the Model 1254 of Telectronics Pacing Systems provide such a setting for diagnostic purposes), both chambers beat simultaneously. Even with a 20 ms AV delay, the beats are approximately simultaneous. The reason for using such a short AV delay is that if there is retrograde conduction, the desire is to reduce its effect by causing the atrial refractory period to begin as late in the overall cycle as possible, i.e., with the retrograde conduction. In this way, any conduction in the reverse direction will arrive at the atria when they are still refractory. Also, causing the atria and ventricles to beat together in step 70 results in collisions of the respective wavefronts and blocks retrograde conduction from occurring in the first place.

If during any of three cycles an A-sense is sensed within the window of the first VP-to-AS interval (see step 63), then a branch is made to step 58 where it is established that there is no retrograde conduction. On the other hand, if in any cycle an A-sense is not detected, then a check is made in step 74 to see whether three cycles have transpired since the initial branch from step 64. If three cycles have not taken place, a branch is made to step 70 where the next pair of atrial and ventricular pacing pulses are generated. When three cycles have transpired without any A-senses having been detected where they previously were detected, i.e., within the window of the first VP-to-AS interval, then it is an indication that the previously detected A-senses (processed in steps 54–64) were indeed due to retrograde conduction. Confirmation takes place in step 76, and the longest VP-to-AS interval is displayed in step 78.

The cycling on the right side of FIG. 2 is particularly important because of the uncertainty inherent in the VP-to-AS interval measurements. Unless there is a way to ensure that A-senses are not the result of noise, the measurements are unreliable, not to mention the determination that retrograde conduction is even present. It is in the final sequencing that a check is made that there is no noise. The simultaneous pacing of the atria and ventricles should result in the VA pathway being refractory so that atrial retrograde beats from ventricular stimuli cannot occur. If atrial senses still occur following simultaneous atrial and ventricular pacing, then the atrial sensed beats must be from other sources (e.g., noise, atrial premature beats, etc.) and there are no atrial beats resulting from retrograde conduction.

The flow chart of FIG. 2 depicts the sequencing for one selected measurement rate (see step 40). Preferably, retrograde conduction measurements may be made at different pacing rates. Succeeding tests at different pacing rates may be performed automatically, rather than to require the physician to program a different pacing rate and to re-initiate the test every time that a new test rate is desired. For example, it is possible to provide a button on the programmer which when operated by the physician automatically increases the rate by 10 pulses per minute, and then re-initiates the test.

It should be noted that in step 52 the pacemaker is programmed to operate in the VVI mode with A-sensing enabled. This in effect converts the VVI mode to a VDI mode. If a particular pacemaker cannot be programmed to the VDI mode, the VDD mode should be used. The difference between the two modes is that in the VDD mode, every A-sense results in the triggering of an AV delay so that V-paces track A-senses. Such tracking is not needed or desired when performing the test sequence. In fact, such tracking can give rise to PMT being induced during the test sequence, and to avoid this from happening the pacemaker should be programmed to have the longest possible PVARP at the selected pacing rate. This will ensure that while A-senses are used to terminate each VP-to-AS interval measurement, they do not trigger AV delays and V-paces.

While in the method depicted in FIG. 2 the measurement process begins under control of the physician via the pacemaker programmer, in the method depicted in FIG. 3 the overall cycling begins with the suspicion of PMT by the pacemaker. As depicted in step 80, PMT is suspected upon the sudden onset of a fast atrial rate together with the other factors discussed above. There are other algorithms for suspecting PMT, and they may also be employed as the first step in the subject invention. The problem with all of them is that they are unreliable. That is why detection and confirmation of the existence of PMT is always desired. This is accomplished in the flow chart of FIG. 3, in steps 82 through 97.

Steps 82–90 in FIG. 3 are comparable to steps 60–66 in FIG. 2. In step 82, a VP-to-AS interval is measured. If it is the first, as determined in step 84, it is saved in step 86 and the next interval is measured. If it is not the first, a test is made in step 88 to see whether five intervals have been measured. If not, a return is made to step 82 for another measurement. After five intervals have been measured, the system moves on to step 90.

Step 90 is similar to step 64 in FIG. 2—the question is whether the VP-to-AS intervals which have just been measured are consistent. If they are not, then it is determined in step 92 that PMT does not exist, despite the fact that it was "suspected" in step 80, and the processing comes to an end. On the other hand, if the measured intervals are consistent, that is not sufficient. Detection and confirmation are still required. Following detection in step 90, confirmation and termination start with step 93.

Steps 93–96 are comparable to same as steps 68–74 in FIG. 2. If simultaneous A-pace and V-pace pulses are generated, and if any A-sense occurs within a window of the first VP-to-AS interval, as determined in step 95, it means that the previous A-senses were most probably not due to retrograde conduction, and a branch is taken to step 92. It is determined that the PMT "suspicion" of step 80 was in error, and the PMT "detection" of step 90 was similarly in error.

Instead of generating simultaneous A-pace and V-pace pulses, it is possible to generate a V-pace immediately after an A-sense. The effect is the same—it makes no difference why the atria contracted.

Care should be exercised when the first pair of simultaneous A-pace and V-pace pulses occur. To avoid generating an A-pace during the refractory period of an immediately preceding retrograde P-wave in the detection process, a delay should be interposed. Preferably, this delay should be the API (atrial protection interval) which is standard in some pacemakers such as the Model 1254 of Telectronics Pacing Systems.

On the other hand, if no A-senses are detected within the window of the first VP-to-AS interval for the three simultaneous atrial and ventricular contractions, then PMT is confirmed in step 97, just as retrograde conduction is continued in step 76 of FIG. 2. The test process itself should actually terminate the PMT—simultaneous atrial and ventricular contractions should do this. To be on the safe side, however, in step 98 the PVARP is programmed to the longest VP-to-AS interval measured in the detection process plus a safety margin. The word "program" in step 98 may have either of two meanings. It is possible for the pacemaker to telemeter out to the physician the results of the testing so that the physician can program a longer PVARP. Of course, the patient may have to wait until he next visits his physician in order for his pacemaker to be re-programmed, and he may again suffer from PMT. Alternatively, the pacemaker may extend the PVARP on its own by a small increment. It is well known in the pacemaker art that pacemakers can self-adjust timing intervals (for example, in trying out different pacing pulse sequences in order to revert tachycardia).

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What is claimed is:

1. A method of automatically detecting and confirming the presence of, and terminating, pacemaker mediated tachycardia (PMT) comprising the steps of:

(a) measuring the interval between a generated ventricular pacing pulse and the succeeding sensed atrial beat (VP-to-AS interval) and repeating said interval measurement on at least one subsequent VP-to-AS interval, (b) detecting PMT by determining whether the measured intervals are consistent, (c) if the measured intervals are consistent, then generating several ventricular pacing pulses approximately simultaneously with atrial contractions, (d) confirming that PMT is present only if, while step (c) is performed, atrial beats are not sensed at the ends of measured intervals consistent with the intervals measured in step (a), and (e) if the presence of PMT is confirmed, then extending the pacemaker PVARP to exceed the longest VP-to-AS interval measured in step (a).

2. A method in accordance with claim 1 wherein in step (d) the presence of PMT is confirmed only if atrial beats are not sensed at the ends of all of the measured intervals following said several approximately simultaneous atrial contractions and ventricular pacing pulses.

3. A method in accordance with claim 2 wherein in step (b) a first V-pace-to-A-sense (VP-to-AS) interval is measured for one ventricular pacing pulse, and it is determined whether X out of Y VP-to-AS intervals are within a window around said one VP-to-AS interval.

4. A method in accordance with claim 3 wherein Y=X+1.

5. A method in accordance with claim 4 wherein, prior to confirming the presence of PMT, the possibility of its presence is suspected by the sudden onset of a fast rate together with the rate being higher than the expected physiological rate by a predetermined percentage.

6. A method in accordance with claim 1 wherein in step (b) a first V-pace-to-A-sense (VP-to-AS) interval is measured for one ventricular pacing pulse, and it is determined whether X out of Y VP-to-AS intervals are within a window around said one VP-to-AS interval.

7. A method in accordance with claim 6 wherein Y=X+1.

8. A method in accordance with claim 7 wherein, prior to confirming the presence of PMT, the possibility of its presence is suspected by the sudden onset of a fast rate together with the rate being higher than the expected physiological rate by a predetermined percentage.

9. A method in accordance with claim 6 wherein, prior to confirming the presence of PMT, the possibility of its presence is suspected by the sudden onset of a fast rate together with the rate being higher than the expected physiological rate by a predetermined percentage.

10. A method in accordance with claim 1 wherein, prior to confirming the presence of PMT, the possibility of its presence is suspected by the sudden onset of a fast rate together with the rate being higher than the expected physiological rate by a predetermined percentage.

11. A method of automatically detecting and confirming the presence of pacemaker mediated tachycardia (PMT) comprising the steps of:

(a) in the event that PMT is suspected, measuring the interval between a generated ventricular pacing pulse and the succeeding sensed atrial beat (VP-to-AS interval), and repeating said interval measurement on at least one subsequent VP-to-AS interval, (b) detecting PMT by determining whether the measured intervals are consistent, (c) if the measured intervals are consistent, then pacing the patient's heart in a manner expected to preclude retrograde conduction, and (d) confirming that PMT is present only if, while step (c) is performed, the pattern of atrial beats sensed is markedly different from the pattern of atrial beats sensed in step (a).

12. A method in accordance with claim 11 wherein in step (d) the presence of PMT is confirmed only if atrial beats are not sensed at the ends of all of the measured intervals following the pacing expected to preclude retrograde conduction.

13. A method in accordance with claim 12 wherein in step (b) a first V-pace-to-A-sense (VP-to-AS) interval is measured for one ventricular pacing pulse, and it is determined whether X out of Y VP-to-AS intervals are within a window around said one VP-to-AS interval.

14. A method in accordance with claim 13 wherein Y=X+1.

15. A method in accordance with claim 14 wherein, prior to confirming the presence of PMT, the possibility of its presence is suspected by the sudden onset of a fast rate together with the rate being higher than the expected physiological rate by a predetermined percentage.

16. A method in accordance with claim 11 wherein in step (b) a first V-pace-to-A-sense (VP-to-AS) interval is measured for one ventricular pacing pulse, and it is determined whether X out of Y VP-to-AS intervals are within a window around said one VP-to-AS interval.

17. A method in accordance with claim 16 wherein Y=X+1.

18. A method in accordance with claim 17 wherein, prior to confirming the presence of PMT, the possibility of its presence is suspected by the sudden onset of a fast rate together with the rate being higher than the expected physiological rate by a predetermined percentage.

19. A method in accordance with claim 16 wherein, prior to confirming the presence of PMT, the possibility of its presence is suspected by the sudden onset of a fast rate together with the rate being higher than the expected physiological rate by a predetermined percentage.

20. A method in accordance with claim 11 wherein, prior to confirming the presence of PMT, the possibility of its presence is suspected by the sudden onset of a fast rate together with the rate being higher than the expected physiological rate by a predetermined percentage.

21. An implantable pacemaker which automatically detects and confirms the presence of, and terminates, pacemaker mediated tachycardia (PMT) comprising:

(a) means for generating ventricular pacing pulses, (b) means for measuring the interval between a generated ventricular pacing pulse and the succeeding sensed atrial beat (VP-to-AS interval), and for repeating said interval measurement on at least one subsequent VP-to-AS interval, (c) means for detecting PMT by determining whether the measured intervals are consistent, (d) means responsive to the measured intervals being consistent for generating several ventricular pacing pulses approximately simultaneously with atrial contractions, (e) means for confirming that PMT is present only if, while said several ventricular pacing pulses are being generated, atrial beats are not sensed at the ends of measured intervals consistent with the intervals measured by said measuring means, and (f) means responsive to the presence of PMT being confirmed for extending the pacemaker PVARP to exceed the longest VP-to-AS interval measured by said measuring means.

22. An implantable pacemaker in accordance with claim 21 wherein said confirming means is operative to confirm the presence of PMT only if atrial beats are not sensed at the ends of all of the measured intervals following said several ventricular pacing pulses.

23. An implantable pacemaker in accordance with claim 21 wherein said determining means operates to determine whether X out of Y VP-to-AS intervals following one VP-to-AS interval are within a window around said one VP-to-AS interval.

24. An implantable pacemaker in accordance with claim 23 wherein Y=X+1.

25. An implantable pacemaker in accordance with claim 21 further including means for suspecting the possible presence of PMT by the sudden onset of a fast rate together with the rate being higher than the expected physiological rate by a predetermined percentage, and means for enabling the automatic confirmation and termination of PMT only responsive to operation of said suspecting and detecting means.

26. An implantable pacemaker which automatically detects and confirms the presence of pacemaker mediated tachycardia (PMT) comprising:

(a) means for generating ventricular pacing pulses, (b) means for measuring the interval between a generated ventricular pacing pulse and the succeeding sensed atrial beat (VP-to-AS interval), and for repeating said interval measurement on at least one subsequent VP-to-AS interval, (c) means for detecting PMT by determining whether the measured intervals are consistent, (d) means responsive to the measured intervals being consistent for pacing the patient's heart in a manner expected to preclude retrograde conduction, and (e) means for confirming that PMT is present only if, while said pacing means operates in a manner expected to preclude retrograde conduction, the pattern of atrial beats sensed is markedly different from the pattern of atrial beats operated on by said measuring means.

27. An implantable pacemaker in accordance with claim 26 wherein said confirming means is operative to confirm the presence of PMT only if atrial beats are not sensed at the ends of all measured intervals following pacing of the patient's heart by said means for pacing in a manner expected to preclude retrograde conduction.

28. An implantable pacemaker in accordance with claim 26 wherein said determining means operates to determine whether X out of Y VP-to-AS intervals following one VP-to-AS interval are within a window around said one VP-to-AS interval.

29. An implantable pacemaker in accordance with claim 28 wherein Y=X+1.

30. An implantable pacemaker in accordance with claim 26 further including means for suspecting the possible presence of PMT by the sudden onset of a fast rate together with the rate being higher than the expected physiological rate by a predetermined percentage, and means for enabling the automatic confirmation and termination of PMT only responsive to operation of said suspecting and detecting means.

* * * * *